United States Patent [19]

Miller, Jr. et al.

[11] Patent Number: 4,658,818
[45] Date of Patent: Apr. 21, 1987

[54] APPARATUS FOR TAGGING AND DETECTING SURGICAL IMPLEMENTS

[76] Inventors: George E. Miller, Jr., 4609 Ashton Dr., Sacramento, Calif. 95825; Jon D. Rice, 418 Pera Dr., Rancho Murieta, Calif. 95683

[21] Appl. No.: 722,967

[22] Filed: Apr. 12, 1985

[51] Int. Cl.$^4$ .............................................. A61F 13/00
[52] U.S. Cl. ................................ 128/303.1; 128/903; 604/362
[58] Field of Search .................... 604/362; 128/303 R, 128/631, 775, 709, 670, 207.14, 207.15, 903, 696, 697, 419 PT, 303.1; 340/573

[56] References Cited

U.S. PATENT DOCUMENTS

| | | | |
|---|---|---|---|
| 3,195,535 | 7/1965 | Westermann | 128/903 |
| 3,212,496 | 10/1965 | Preston | 128/903 |
| 3,688,092 | 8/1972 | Shlisky | 128/419 PT |
| 3,768,459 | 10/1973 | Cannon et al. | 128/775 |
| 3,780,727 | 12/1973 | King | 128/697 |
| 3,800,801 | 4/1974 | Gaillard | 128/419 P |
| 3,991,748 | 11/1976 | Ohlssoh | 128/709 |
| 4,184,485 | 1/1980 | Agoston | 128/670 |
| 4,281,664 | 8/1981 | Duggan | 128/696 |
| 4,344,436 | 8/1982 | Kubota | 128/207.15 |

Primary Examiner—Henry J. Recla
Attorney, Agent, or Firm—Lothrop & West

[57] ABSTRACT

An active system for tagging and detecting a surgical implement accidentally left within a patient after the completion of a surgical procedure. A miniature electrical oscillator is attached to each implement and actuated before surgery begins. The pulsed output of each oscillator is coupled to the body's internal fluids and tissue. Before the patient is sutured, a detector, located externally from the body, is employed to sense the pulses from any remaining implements. In the event such pulses are sensed, a sensory alert is actuated and corrective action taken.

8 Claims, 8 Drawing Figures

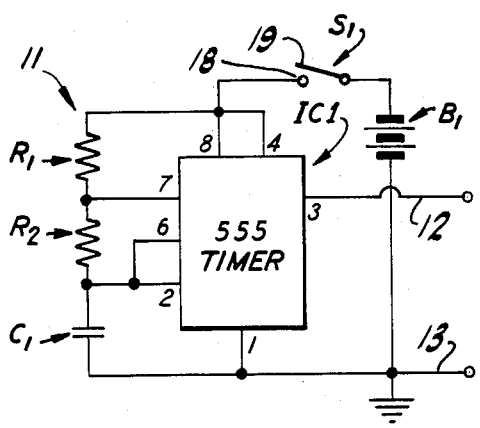
FIG_1
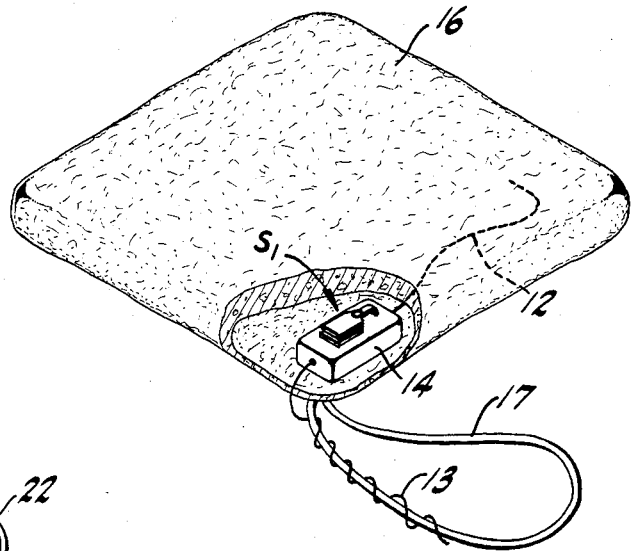
FIG_2
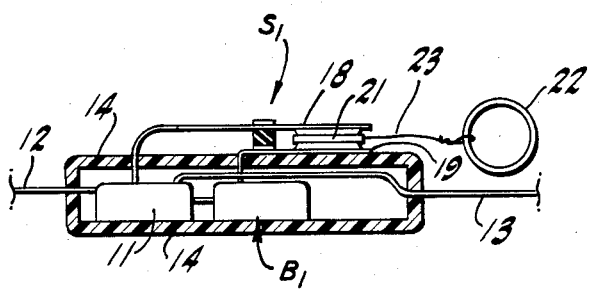
FIG_3
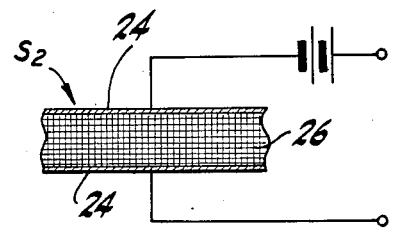
FIG_4
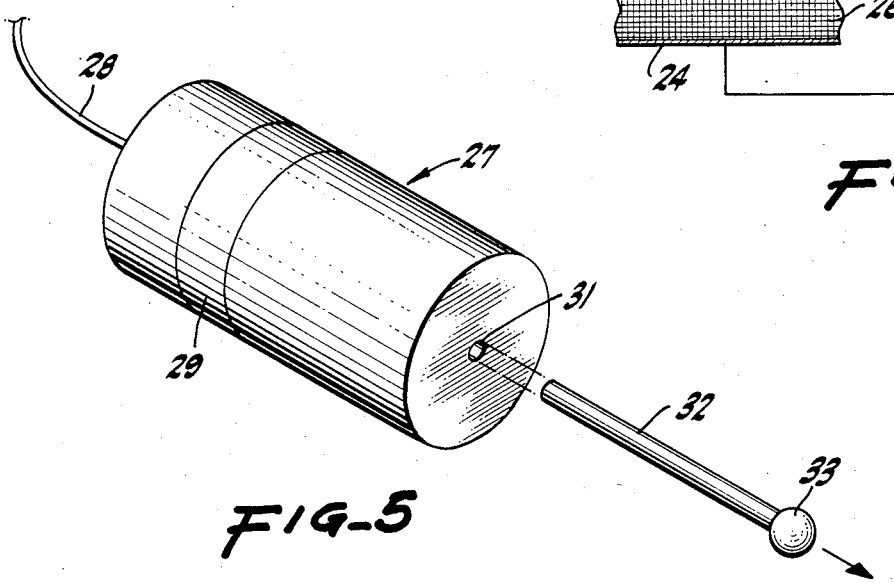
FIG_5

APPARATUS FOR TAGGING AND DETECTING SURGICAL IMPLEMENTS

BACKGROUND OF THE INVENTION

1. Field Of The Invention

The invention relates generally to devices and methods employed to prevent the accidental implantation of surgical implements used in the course of a surgical procedure. More specifically, the invention employs an active surgical implement tagging and detection system, adapted to sense the presence of retained implements before post-operative suturing takes place.

2. Description Of The Prior Art

Known prior art devices and methods used to detect retained surgical implements can generally be classified as "passive" in nature. For example, X-ray examination has long been advocated as a useful means to detect the presence and location of radio opaque implements and radio opaque tags or thread attached to surgical sponges and gauze, or the like. Representative art disclosing such an approach is U.S. Pat. No. 2,698,270 issued to Mesek and U.S. Pat. No. 3,698,393 granted to Stone. X-ray examination of patients does provide fairly reliable screening for retaining articles. However, each screening requires the cumbersome task of moving the X-ray machine into place over a properly positioned patient, whose wound has already been sutured to avoid sterility problems. In the event that a retained implement is discovered, it is necessary to reopen the wound, remove the implement, and then resuture the wound before the patient can be released from anesthesia. In view of the foregoing, X-ray examination for retained surgical implements has not proved practical as a regular procedure.

Other passive systems proposed preferably use a hand manipulable detector to sense the presence of metal, magnetized particles, or radioactive material attached to or associated with the surgical implements. Prior art from among this group includes U.S. Pat. Nos. 3,097,649; 3,422,816; and 3,587,583. While this approach allows examination of the patient in the operating room, health hazards are posed by the radioactive material, and the extraneous metal and magnetic responses present in the operating room make the other systems less than completely reliable.

More recently, in U.S. Pat. Nos. 4,114,601 and 4,193,405, Abels teaches the tagging of surgical implements with a small film deposition of ferrite or other semiconductor material exhibiting gyromagnetic resonance at selected frequencies. When exposed to electromagnetic radiation at two selected frequencies, a higher order product frequency is radiated and detected by an RF receiver. While the Abels device is claimed to work at any frequency, the proposed range of frequencies discussed in the patents is 4.5–5 Gigahertz. It is well recognized that human tissue is significantly absorptive of radio frequency energy at this microwave frequency, and even the 0.5 watt transmitter power range proposed in Abels could present a health hazard either to the patient or to the administrator of the test.

Consequently, while the "passive" approach is initially appealing in terms of the simplicity and the diminutive size of the surgical implement tag or identifier, other problems are posed by the cost, safety and reliability of the transmission and detection systems used to sense the presence of passive tags.

SUMMARY OF THE INVENTION

The invention herein is generally active in nature, employing the use of a miniature, battery powered oscillator attached to each implement and actuated prior to initial use during the course of the surgical procedure. The output of the low powered oscillator is coupled to the body fluids and tissue of the patient by unobtrusive conductors located on the oscillator's housing or physically integrated with the implement's structure.

The frequency of the oscillator is selected safely to exceed the normal physiological signals of the body, so as not to interfere with the usual electro-cardiograpic monitoring of the patient's condition during surgery. In the lower range of useful oscillator frequencies, say 4 KHZ, the patient's body fluids and tissue conduct the oscillator pulses with reasonable efficiency. Consequently, post-operative detection of the oscillator's pulses may be effected by momentarily switching the ouput of the patient's ECG electrodes from the ECG monitor to the pulse detection system.

The detector employs amplification, filtering, and in some cases, logic circuitry to produce an output signal in the event that a surgical implement is retained within the patient's body. The detector's output is then fed to an alert system, providing visual and aural indications to the test administrator that corrective action is needed. The use of such low frequencies is advantageous in that it effectively integrates the implement tagging and detection system with existing ECG hardware and associated personnel.

In the event that a tagging oscillator operating at a higher frequency is employed, say within the range of 1–30 MHZ, the output signal is similarly coupled to the body fluids and tissue, but the resultant signal is detected in a somewhat different fashion than just described.

It has been determined that body-coupled radio frequency energy, at least within in the 1–30 MHZ range, is directly radiated by the patient's body to a significant extent. Thus, an inductive loop or other wire antenna passed over the patient's body has proven effective in intercepting the oscillator's radiated pulses and locating the surgical implement. The low level output of the inductive loop is fed through amplifier, filtering, and logic circuitry similar to that employed in the low frequency detector, and any detected pulses actuated an interconnected alarm or alert system.

Specific aspects of the invention's construction and operational features, including variations thereof, will be described more fully in the drawings and detailed description of the preferred embodiment to follow.

BRIEF DESCRIPTION OF THE DRAWINGS

FIG. 1 is a schematic diagram of a typical low frequency tagging oscillator, operating at approximately 4 KHZ;

FIG. 2 is a perspective view of a surgical sponge, a corner portion thereof being broken away to reveal the tagging oscillator and associated output electrodes;

FIG. 3 is a longitudinal, cross-sectional view of the tagging oscillator taken to an enlarged scale, showing the inner details and the pull ring switch prior to actuation;

FIG. 4 is a schematic diagram of a saline fluid actuated switch and associated battery power supply;

FIG. 5 is a perspective view of an alternative housing, or package, for the tagging oscillator, showing the pin acutation switch in a withdrawn position;

DETAILED DESCRIPTION OF THE PREFERRED EMBODIMENT

Figure 6:
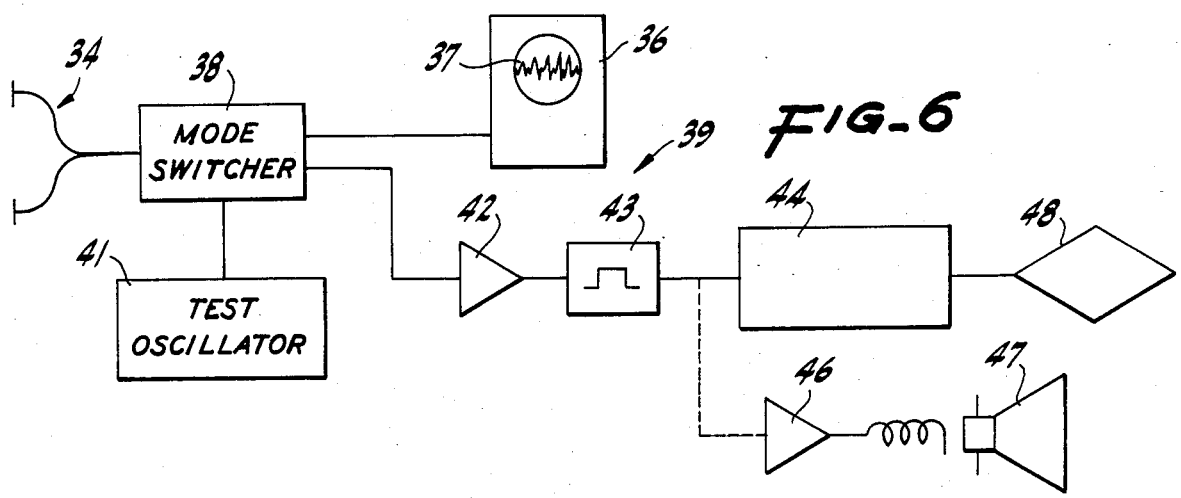
FIG. 6 is a block diagram of a low frequency detection and alert system, shown in combination with a mode switcher, test oscillator, and a conventional ECG electrode and monitoring system.

Turning now to FIG. 1, a low frequency tagging oscillator 11 is shown. The oscillator 11 is of conventional design, employing the widely used 555 timer chip, IC 1. R1, R2, and C1, are valued respectively at 11 K ohm, 11 K ohm, and 0.005 uF, providing a characteristic oscillator output frequency of approximately 4 KHZ. The oscillator's frequency is not critical per se, but extremely low frequencies, especially those below 100 HZ, should be avoided. Since the body's normal physiological signals are within this extremely low frequency range and are being monitored by ECG equipment during surgery, interference with ECG monitoring can only be avoided by selecting an oscillator frequency safely above 100 HZ.

It is proves desirable to raise the oscillator's frequency into the Megahertz range, an alternate oscillator and detection system may be employed, and such a high frequency system will be described in detail following the present discussion of the low frequency system.

Typically, the battery B1, and the entire circuitry of the oscillator 11, with the possible exception of the switch S1, are enclosed within a plastic or elastomeric housing or container 14 (see FIGS. 2 and 3). By sealing the oscillator circuity within such a container, reliable operation of the circuit will be ensured despite immersion in body fluids, handling during surgical procedures, and subjection to electrocautery activity in the immediate area. So enclosed, the external dimensions of the oscillator package would typically assume the compact figures of 0.5 cm × 1 cm × 2 cm.

The output electrodes 12 and 13 are constructed from an electrically conductive material, and extend exteriorly from the housing 14. Depending upon the particular housing design or implement to be tagged, the output electrodes 12 and 13 can assume a variety of configurations. The tagged item in FIG. 2 is a surgical sponge 16, or gauze, including a loop 17 to facilitate removal of the sponge from the patient's body. Utilizing the loop 17 to good advantage, the output electrode 13 is readily wound around or intertwined with a portion of the loop, providing ready exposure to the patient's body fluids and tissue. The other electrode 12 extends within the body of the sponge 16, again providing good coupling to the patient's body, particularly when the sponge is fluid saturated. The generally saline character of internal body fluid enhances the coupling of the oscillator signal to the patient's body. However, since the power levels are extremely low and the frequency is far removed from the potentially dangerous microwave region, no safety hazard is posed either to the patient or to the surgical team.

Actuating switch S1 is connected in series with battery B1, providing low voltage power to the oscillator 11 prior to the initial use of the sponge 16. The actuating switch S1 can variously be adapted to suit the nature and size of the surgical implement in connection with which it is used. Considering the first, the actuating switch S1 disclosed in FIG. 3, a pair of inwardly spring biased terminals 18 and 19 is shown separated by a non-conductive tab 21. A small pull ring 22 is attached to the tab 21 by means of a short piece of cord 23, or string. The ring 22 extends exteriorly from the sponge 16, for ready access. The tab 21 is removed by grasping and pulling on the ring 22, allowing terminals 18 and 19 to interconnect, thereby applying actuating power to the oscillator 11.

An alternative fluid actuated switch S2, shown in FIG. 4, incudes a pair of conductor plates 24 bridged by a porous wick 26. The spacing of the plates 24 is such that when the porous wick is immersed within a saline solution, such as body fluids, a path of sufficiently low resistance is formed, and the oscillator 11 will begin operating. While any implement remaining within the body cavity for a prolonged period will be totally wetted by body fluids, the placement and retention period of a particular implement prior to wound closure may be such that the wick 26 does not become adequately saturated. In this event, the oscillator 11 may not be active during the implement detection period. Accordingly, to ensure positive actuation in every instance, it may be desirable to dip the wick 26 within a separate saline solution prior to initial use of the tagged implement.

Once actuated, the tagging oscillator 11 draws continuously upon the battery B1, for its sole source of power. The drawing current of the oscillator 11 and the power capacity of the battery B1, are such that reliable operation of the oscillator should be provided for approximately ten hours, or so. While ten hours of oscillator operation should be sufficient for almost all surgical procedures, alternative circuitry for the oscillator could extend this period substantially. Rather than running the oscillator continuously, a series of say three to five pulses followed by a quiescent period of five seconds, or so, would lower the duty cycle of the oscillator and prolong battery life even further.

Pulsed or gated operation of the tagging oscillator can be accomplished in a variety of ways. A control, low power oscillator, running at a low frequency, could be used to switch power on and off to the secondary, or high power oscillator circuitry. Alternatively, an RC circuit could be employed in combination with a voltage limiting diode for establishing a charge/discharge cycle which would pulse the operation of the tagging oscillator. Thus, while the basic, continuously running oscillator 11 is shown for illustrative purposes, many variations both in the duration and pattern of oscillator pulses produced by alternative circuitry are contemplated, and such circuitry is sufficiently well understood in the art so as not to require further detailed explanation herein.

Aside from reducing the size and enhancing the life of the battery powering the tagging oscillator, pulsed oscillator operation provides a further identifier for the apparatus used to sense the pulses and distinguish them from extraneous noise. This feature will be discussed more fully in the explanation of the detector apparatus, to follow herein.

Returning briefly to FIG. 3, the oscillator 11 and the battery B1, are shown contained within the elongated housing 14. The output electrodes 12 and 13 are flexible wire conductors, extending exteriorly from either end of the housing 14 physically to integrate with elements of the sponge 16, as explained previously. While this type of packaging is well suited for a sponge, other surgical implements may require alternative packaging for the tagging oscillator and associated components.

FIG. 5 illustrates oscillator, battery, and switch packaged within a cylindrical capsule 27, constructed from a plastic or elastomeric material as described before. A wire electrode 28 extends from one end of the capsule 27, to connect or merge with a physical feature of the tagged implement. A band electrode 29 extends circumferentially around the capsule 27, providing the second electrode for coupling the pulsed output of the internal oscillator and battery (not shown) to the body's fluids and tissue.

An aperture 31 is provided at the other end of the capsule 27, to accommodate a non-conductive actuating pin 32. Prior to actuation of the tagging oscillator, the pin 32 extends interiorly into the capsule 27, maintaining a pair of spring-biased switch contacts (not shown) in spaced relation. When it becomes necessary to activate the tagging oscillator, a knob 33 on the outer end of the pin is grasped, and the pin is withdrawn from the capsule 27, as shown in FIG. 5. The internal switch contacts are thereby allowed to spring together, actuating the oscillator.

It is apparent that a second band electrode could be used in lieu of the wire electrode 28. The second band electrode would extend circumferentially around the capsule 27 and be spaced from the first band electrode 29. Such a packaging and electrode combination may be desirable for tagging an unusually small surgical implement.

Prior to the commencement of surgery, and in any event prior to the use of a particular surgical implement in the course of surgery, the tagging oscillator of each implement is actuated. After the surgery has been completed, but before the post-operative suturing takes place, the patient is checked for any surgical implements that may have accidentally been overlooked and retained within the surgical cavity. Accordingly, a detection system, located outside the body of the patient, is used to sense and check for oscillator pulses from any such retained implements.

Making reference now to FIG. 6, a pair of electrocardiographic (ECG) electrodes 34 is generally used in connection with an ECG monitor 36, during the course of any significant surgical procedure, to observe the physiological signals of the patient's cardiovascular system. Normal physiological signals are below 100 HZ, and the monitor 36 is designed to display such signals on a cathode ray tube 37. The invention herein contemplates the use of a mode switcher 38 to allow use of the existing ECG electrodes 34 as sensors for the oscillator detector, generally designated by reference numeral 39.

More specifically, the mode switcher 38 would include a normal position for surgical ECG monitoring and a detect position for directing the output of the ECG electrodes to the input of the detector 39. It may also be desirable for the mode switcher 38 to have a third test positon, for directing the output of a 4 KHZ test oscillator 41 to the input of the detector 39, to confirm proper operation of the detector 39 before the post-operative, implement detection procedure begins. Operation of the ECG system would be unaffected during the detector testing procedure.

Assuming that normal operation of the detector 39 is confirmed, the mode switcher 38 is switched to the detect position, and the pulses of any retained tagging oscillators will be routed to the amplifier 42. The output of the amplifier 42 is conditioned by a bandpass filter 43, having in this case a center bandpass design frequency of 4 KHZ. The use of a bandpass filter designed for the frequency of the tagging oscillator ensures that all extraneous noise, including the body's physiological signals, will be severely attenuated.

Detection of a signal present at the output of the filter 43 can be accomplished any number of ways. If the oscillator frequency is within the audio frequency range, such as here, the signal could be raised by amplifier 46 to levels necessary to drive a loudspeaker 47. This would provide a direct aural indication that an implement had been retained, and that corrective action should be taken to locate the implement.

While such direct detection can easily be accomplished, it may be desirable to subject the signal to further testing and processing before exploration for the implement begins. Accordingly, an amplifier/comparator 44 is provided to reject signals passing through the filter 43 that do not exceed a predetermined level. If the signal did exceed the predetermined level, it would then pass to the alarm 48.

In its most basic form, the alarm 48 would provide direct aural and/or visual indications to the test administrator that an implement search should be initiated. A latching circuit could also be provided to lock on the indicators until such time as the latch was reset.

If the tagging oscillator were designed to provide pulsed output, as previously discussed, the alarm 48 could include counter circuitry to collect information about the incoming signal during a predetermined test period. At the end of the period, the counter would be read and compared to established data for tagging oscillators. If the collected information and established data correlated, the indicators would be activated.

It would also be possible to eliminate the mode switcher 38, and provide an independent set of electrodes, attached to the patient's body. However, it is believed that the dual utilization of the ECG hardware is the preferred manner of practicing the low frequency version of the invention.

Figure 7:
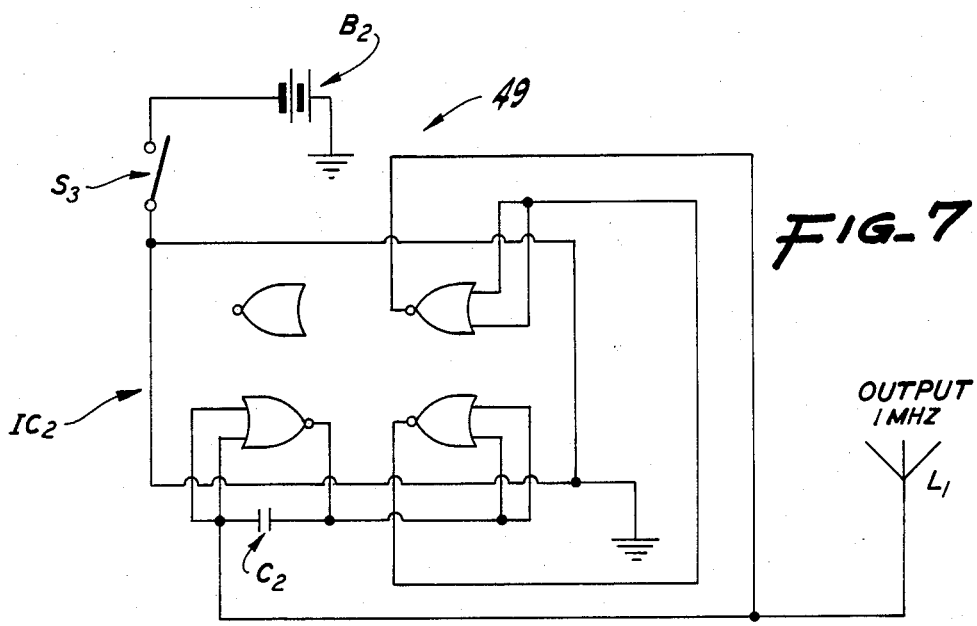
FIG. 7 is a schematic diagram of a typical high frequency tagging oscillator, operating at approximately 1 MHZ; and, FIG. 8 is a block diagram of a high frequency detection and alert system.

In the event that a higher oscillator frequency is chosen, the tagging and detection system operates in basically the same fashion, but several differences in the hardware and detection procedure are noted herein. Making specific reference to FIG. 7, a high frequency tagging oscillator 49 is shown, utilizing a CMOS "ring oscillator", IC2. Battery B2 and switch S3 are similar to the battery and switch constructions already discussed. Capacitor C2, having a value of 0.01 uf, was selected to provide a characteristic oscillator output frequency of 1 MHZ. The output of the oscillator is fed to an "antenna", L1. Various configurations of L1 would be useable, ranging from a length of wire wound in serpentine fashion through or about the implement, to a small coil of wire wound upon a form. In any event, L1 is effective to couple the output of oscillator 49 into the patient's body tissue and fluids. Again, owing to the very low output and relatively low RF frequency of the oscillator 49, no health hazard is posed.

It has been determined that as the frequency of the tagging oscillator is raised into the RF range (here, 1 MHZ), the output of the oscillator coupled to the body is radiated by the body, and can therefore be effectively detected without the need of any direct physical interconnection.

Figure 8:
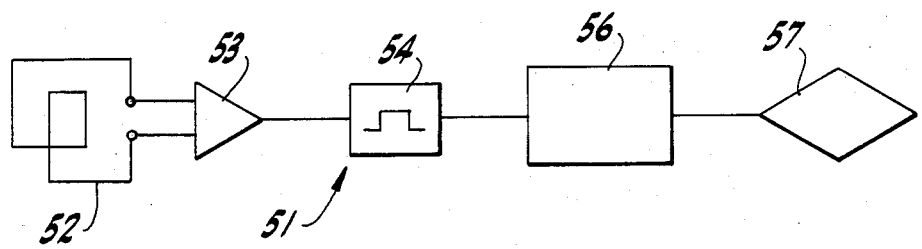

Accordingly, the high frequency receiver 51, or detector, shown in FIG. 8 employs a loop of wire receiving antenna 52 to sense pulses radiated from the patient's body. The receiving antenna 52 could vary from a simple one-turn U-shaped loop or whip, to a multi-turn loop antenna having directional characteristics. The output of the receiving antenna 52 is fed to an amplifier 53, a bandpass filter 54, a diode detector and smoothing network 56, and an alarm 57. It is evident that the comparator, latching, and counter circuitry previously discussed in connection with the low frequency detector could be adapted to the receiver 51 to perform analogous functions. It is contemplated that the entire receiver 51, including the alarm 57, could be packaged into a hand-held unit, capable of being passed over the patient's body for ready detection of any tagged surgical implements.

It will be appreciated that we have provided an active surgical implement tagging and detection system which is adaptable to a wide variety of operating room requirements and which provides the necessary levels of reliability and safety.

What is claimed is:

1. An apparatus for detecting a surgical implement retained within a surgically exposed human body cavity, the apparatus comprising, in combination:
    (a) tagging means adapted to be attached to a surgical implement insertable within a human body cavity, and including:
        (1) oscillator means for producing a series of electrical output pulses, said pulses having a frequency selected safely to exceed the normal physiological signals of a body into which an associated surgical instrument is to be inserted when actuated prior to insertion of an associated surgical instrument within a surgically created body cavity; and
        (2) conductor means attached to the oscillator means for electrically conductively coupling the electrical output pulses of the oscillator means to internal body fluids and tissue of a human body into which a surgical instrument associated with the oscillator means is inserted; and
    (b) detecting means located externally of a human body into which is inserted a surgical implement provided with a tagging means, and including:
        (3) reception means for receiving a signal from a tagging means, said reception means including means for rejecting the normal physiological signals of the human body;
        (4) detector means attached to the reception means for sensing a signal received from a tagging means; and
        (5) alert means attached to the detector means for providing a sensory response whenever a signal from a tagging means is sensed.

2. A system as in claim 1 in which said detector means includes at least two electrodes and an amplifier, one end of said electrodes being attached to respective points upon an associated body and the other end of said electrodes being interconnected to the input of said amplifier.

3. A system as in claim 2 further including bandpass filter means responsive to the output of said amplifier for attenuating extraneous signals substantially removed from the frequency of said electrical pulses.

4. A system as in claim 2 in which the frequency of said electrical pulses is substantially higher than normal human physiological signals, and further including switching means having an ECG monitor mode in which the output of said electrodes is directed to the input of an electrocardiographic monitor, and a detection mode in which the output of said electrodes is directed to the input of said amplifier.

5. A system as in claim 2 in which the frequency of said electrical pulses is substantially higher than normal physiological signals, and further including an electrocardiographic monitor connected across the input of said amplifier, for displaying the ECG signal of an associated body, concurrently and independently from the operation of said amplifier.

6. A system as in claim 1 in which said detector means includes inductive loop means interconnected to an amplifier, said inductive loop means being moved into relative proximity with said conductive means for sensing the electrical pulses coupled to and radiated by the body.

7. A system as in claim 6 further including bandpass filter means responsive to the output of said amplifier for attenuating extraneous signals substantially removed from the frequency of said electrical pulses.

8. A system as in claim 7 in which the frequency of said electrical pulses is at least 1 MHZ.

* * * * *